United States Patent [19]

Bouvet et al.

[11] 4,296,034
[45] Oct. 20, 1981

[54] POLYFLUORINATED SULFONAMIDES

[75] Inventors: Pierre Bouvet, Rouen; Jean-Pierre Lalu, La Mulatiere, both of France

[73] Assignee: Produits Chimiques Ugine Kuhlmann, Paris, France

[21] Appl. No.: 41,926

[22] Filed: May 24, 1979

Related U.S. Application Data

[63] Continuation of Ser. No. 466,051, May 1, 1974, abandoned, which is a continuation of Ser. No. 5,352, Jan. 23, 1970, abandoned.

[30] Foreign Application Priority Data

Jan. 22, 1969 [FR] France .................. 69 01059

[51] Int. Cl.³ ............... C07D 295/22; C07C 143/75; C07C 143/74
[52] U.S. Cl. .................. 260/326.82; 564/96; 564/97; 252/542; 252/545
[58] Field of Search .......... 260/556 F, 556 A, 326.82; 564/96, 97

[56] References Cited

U.S. PATENT DOCUMENTS 2,615,000  10/1952  Bradley .................. 260/556 A
3,458,571   7/1969  Tokoli ..................... 260/561 HL
3,829,466   8/1974  Staffe ..................... 260/556 F

OTHER PUBLICATIONS

Bouvet et al.; Chem. Abs. 73, 109275 (1970).

Primary Examiner—Mark L. Berch
Attorney, Agent, or Firm—Pennie & Edmonds

[57] ABSTRACT

This invention pertains to polyfluorinated sulfonamides having the formula

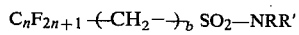

$$C_nF_{2n+1}\text{---}(CH_2\text{---})_b\,SO_2\text{---}NRR'$$

wherein n is a number of from 1 to about 20; b is an integer of from 2 to about 20; R is selected from the group consisting of a hydrogen radical and an alkyl radical having from 1 to about 10 carbon atoms; and R' is selected from the group consisting of a hydrogen radical, an alkyl radical of from 1 to about 10 carbon atoms, a cyclic alkyl radical of from 5 to 12 carbon atoms, and an aryl radical of from about 6 to 12 carbon atoms. These compounds are prepared through the action of polyfluorinated sulfonic chloride on an amino derivative.

2 Claims, No Drawings

POLYFLUORINATED SULFONAMIDES

This is a continuation of application Ser. No. 466,051 filed May 1, 1974, abandoned, which in turn is a continuation of application Ser. No. 5,352, filed Jan. 23, 1970, now abandoned.

SUMMARY OF THE INVENTION

This invention relates to the field of industrial sulfonamides. Briefly, these compounds have found extensive usage as auxiliary ingredients in the formulation of products useful in the textile, leather, and paper industries. For example, these compounds serve as surface active agents and as leveling agents for use in waxes, greases, varnishes and paints. It has been found that the polyfluorinated sulfonamides of the present invention are especially suited to these uses.

Briefly stated, the present invention relates to polyfluorinated sulfonamide compounds and the method of their preparation. The compounds of this invention have the structure $$C_nF_{2n+1}\text{-(CH}_2\text{)}_b\text{-SO}_2\text{-NRR'}$$

in which:
(a) $C_nF_{2n+1}$ corresponds to a straight or branched polyfluorinated carbon chain, n being a number of from 1 to 20;
(b) b is an integer of from 2 to 20, and preferably equal to 2 or 4;
(c) R is a radical selected from the group consisting of hydrogen and alkyl radicals containing from about 1 to 10 carbon atoms;
(d) R' is a radical selected from the group consisting of (1) hydrogen, (2) alkyl radicals containing from about 1 to 10 carbon atoms, (3) cyclic alkyl radicals containing from about 5 to 12 carbon atoms, and (4) substituted and non-substituted aryl radicals containing from about 6 to 12 carbon atoms; and
(e) the group NRR' can consist of a cyclic amine radical containing from 4 to 8 carbon atoms, for example the pyrrolidine radical

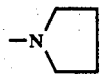

These new and useful compounds are prepared by reacting a polyfluorinated sulfonic acid halide with ammonia, a primary amine, or a secondary amine.

DESCRIPTION OF THE PREFERRED EMBODIMENTS

The reaction proceeds according to the equation

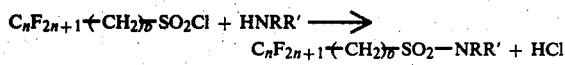

The temperature range best suited for the reaction is from about 1° to 150° C. Usually the reaction is exothermic and external heat is not required. In this case it is preferable to begin the reaction at ambient temperature. However, in some instances the reaction is not appreciably exothermic (for instance when HNRR' is aniline) or the polyfluorosulfonylchloride $[C_nF_{2n+1}\text{-(CH}_2\text{)}_b\text{-SO}_2Cl]$ is not completely soluble in a solvent, and a means of heating the reaction mixture may be resorted to.

It is preferable to use a solvent, but this is not indispensable. The solvent must be inert with regard to the reagents involved. Such solvents which are suitable include ethers such as ethyl ether, isopropyl ether, tetrahydrofuran; esters such as ethyl acetate, ethyl formate; halogenated hydrocarbons such as chloroform, carbon tetrachloride, methylene chloride, trichloro-1,1,2-trifluoroethane, and other solvents which satisfy the requirement of inertness stated supra.

The ratio of the reagents in mol of HNRR' per mol of $C_nF_{2n+1}\text{-(CH}_2\text{)}_b\text{SO}_2Cl$ is preferably at least equal to 2 in order to neutralize the hydrochloric acid liberated during the reaction.

The following examples are provided to further point out and describe various embodiments of the present invention. These examples are not intended to limit the invention in any way.

EXAMPLE 1

$C_2F_5$—$C_2H_4$—$SO_2Cl$ (12.3 g; 0.05 mol) was dissolved in ethyl ether (100 cm$^3$) and ammonia was added gradually to the solution, while stirring, at the rate of 7.1 l per hour for 2 hours. At the beginning of the addition of ammonia, a white solid substance was immediately formed. During the first 15 minutes the temperature increased from 20° to 35° C. and remained at 35° C. for 1 hour before gradually receding to 25° C. When the reaction was complete, the reaction medium was washed in three 100 ml. portions of water. The ethereal portion was then dried with anhydrous sodium sulfate which was removed by filtration before evaporating the ethyl ether. In this manner 11.7 g of solid matter was obtained, which upon recrystallization from 100 cm$^3$ of a mixture of carbon tetrachloride (95% by volume) and ethyl acetate yielded 10.3 g of $C_2F_5$—$C_2H_4$—$SO_2NH_2$.

This sulfonamide was obtained in a yield of 90.5%.

EXAMPLE 2

34.6 g of $C_4F_9$—$C_2H_4$—$SO_2Cl$ was dissolved in 100 cm$^3$ of ethyl ether and ammonia (15 l/h) was added to the solution, while stirring for a period of 2 hours. At the beginning of the addition of ammonia, a white solid substance was immediately formed. In the course of the first 10 minutes of adding ammonia, the temperature rose from 20° to 34° C., and it remained at 34° C. for 45 minutes before dropping gradually to 25° C. When the reaction was finished, ethyl ether (200 cm$^3$) was added to the reacting medium and the resulting solution was washed successively in three 100 ml. portions of water. The ethereal portion was then dried on anhydrous sodium sulfate, which was removed by filtration before the evaporation of ethyl ether. In this manner 32.8 g of solid matter was obtained, which upon recrystallization in 50 cm$^3$ of a mixture of carbon tetrachloride (90% by volume) and ethyl acetate, gave 30.1 g of $C_4F_9$—$C_2H_4$—$SO_2$—$NH_2$ having a melting point of 47°–49° C. The yield was 92%.

EXAMPLE 3

50 g of $C_6F_{13}$—$C_2H_4$—$SO_2Cl$ was dissolved in 100 cm$^3$ of ethyl ether, and ammonia (7 l/h) was added to the solution, while stirring for a period of 2 hours. Immediately on the addition of ammonia, a white, solid substance formed. During the first 15 minutes of adding ammonia, the temperature rose from 20° to 35° C. and it remained at 35° C. for 1 hour before gradually dropping to 25° C. When the reaction was finished, the procedure of Example 1 was followed and 43 g of a solid substance having a melting point of 90°–93° C. was obtained. This solid matter was recrystallized in 150 cm³ of a mixture of carbon tetrachloride (90% by volume) and ethyl acetate and 39.1 g of C₆F₁₃—C₂H₄—SO₂—NH₂ having a melting point of 92°–93° C. was recovered.

The yield was 81.5%.

EXAMPLE 4

44.6 g of C₆F₁₃—C₂H₄—SO₂Cl was dissolved in 200 cm³ of ethyl ether and 17.5 g of methylamine was added while stirring over a period of 2.5 hours. Immediately upon the addition of methylamine, a solid was formed. The temperature rose from 25° C. to 34° C. in 30 minutes and stabilized at this temperature for 45 minutes before dropping gradually to 25° C. When the reaction was finished, the reacting medium was washed successively in three 200 cc portions of water. The ethereal solution was dried on anhydrous sodium sulfate which was separated by filtration. Evaporation of the ether yielded 42.3 g of solid matter, which was recrystallized in 150 cm³ of a mixture of carbon tetrachloride (90% by volume) and ethyl acetate. 41.5 g of C₆F₁₃—C₂H₄—SO₂—NH—CH₃ having a melting point of 80°–81° C. was obtained.

The yield amounted to 94%.

EXAMPLE 5

22.3 g of C₆F₁₃—C₂H₄—SO₂Cl was dissolved in 100 cm³ of ethyl ether and to the constantly stirred solution was added 9.8 g of aniline over a period of 30 minutes. Immediately after the addition of aniline, a white, solid substance was formed. The reacting medium was heated to 35° C. for 1.5 hours. When the reaction was finished the procedure of Example 1 was followed and 24.7 g of solid matter was obtained which was recrystalized in 50 cm³ of carbon tetrachloride. 23.4 g of

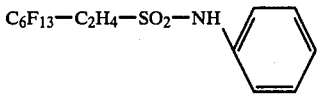

having a melting point of 64°–66° C. was isolated.

The yield was 93%.

EXAMPLE 6

22.3 g of C₆F₁₃—C₂H₄—SO₂Cl was dissolved in 100 cm³ of ethyl ether and to the constantly stirred solution was added 10.4 g of cyclohexylamine over a period of 30 minutes. At the outset, a solid, white substance was formed. The temperature rose from 20° to 35° C. and it remained at 35° C. for 30 minutes before dropping gradually to 25° C. after 2 hours. When the reaction was finished, the procedure of Example 1 was followed and 24.4 g of solid matter was isolated upon recrystallization in 150 cm³ of hexane 23.9 g of

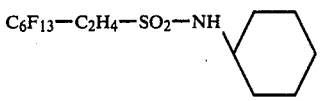

having a melting point of 66°–68° C. was recovered.

The yield attained 94%.

EXAMPLE 7

22.3 g of C₆F₁₃—C₂H₄—SO₂Cl was dissolved in 100 cm³ of ethyl ether and to the constantly stirred solution was added 7.5 g of pyrrolidine for a period of 30 minutes. Immediately upon the addition of pyrrolidine, a white, solid substance formed. The temperature rose from 20° C. to 34° C. in 15 minutes and stabilized at this temperature for 20 minutes and then dropped gradually to 23° C. after 2 hours. When the reaction was finished, 500 cm³ of ethyl ether was added and the solution which resulted was washed successively with two 100 cm³ portions of water. After drying and evaporating as in Example 1, 23.1 g of solid matter was isolated. This was recrystallized in 200 cm³ of a mixture of carbon tetrachloride (90% by volume) and ethyl acetate. 20.6 g of

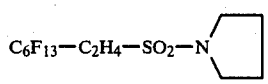

having a melting point of 97°–99° C. was obtained.

The yield amounted to 86%.

EXAMPLE 8

22.3 g of C₆F₁₃—C₂H₄—SO₂Cl was dissolved in 100 cm³ of ethyl ether and to the constantly stirred solution was added 717 g of diethylamine. Immediately a solid, white substance formed. The temperature rose from 20° to 35° C. in 20 minutes and stabilized at this temperature for 20 minutes and then dropped gradually to 25° C. after 2 hours. When the reaction was finished, the procedure of Example 1 was followed and 23.1 g of solid matter was obtained which was then recrystallized in 50 cm³ of hexane. 21.9 g of C₆F₁₃—C₂H₄—SO₂—N(C₂H₅)₂ having a melting point of 68°–70° C. was isolated.

The yield was 91%.

EXAMPLE 9

136.5 g of C₈F₁₇—C₂H₄—SO₂Cl was added to 500 cm³ of ethyl ether and to the constantly stirred mixture ammonia was added for 4 hours at a rate of 15 l/h. The temperature rose from 20° to 34° C. in 20 minutes and stabilized at this temperature for 1½ hours before dropping gradually to 23° C. The ethyl ether was removed through evaporation leaving a solid substance which was washed successively with two 400 cm³ portions of ethyl acetate. After filtration the filtrate was recovered and concentrated to 250 cm³. Then 250 cm³ of carbon tetrachloride was added, resulting in recrystallization of C₈F₁₇—C₂H₄—SO₂—NH₂. 117.5 g of C₈F₁₇—C₂H₄—SO₂—NH₂ having a melting point of 143°–146° C. was recovered.

The yield was 89%.

EXAMPLE 10

27.3 g of C₈F₁₇—C₂H₄—SO₂cl was dissolved in 100 cm³ of ethyl ether and over a period of 2 hours 8.5 g of methylamine was added to the constantly stirred solution. A solid, white substance formed as soon as the methylamine was introduced. The temperature rose from 20° to 34° C. in 20 minutes and stabilized at this temperature for 45 minutes before gradually dropping to 25° C. Ethyl ether was then removed by evaporation and a solid substance was obtained which was extracted with 200 cm³ of ethyl acetate. The extraction solution was filtered and the ethyl acetate evaporated yielding 25.2 g of solid matter which was recrystallized in 100 cm³ of a mixture of carbon tetrachloride (90% by volume) and ethyl acetate. 23.2 g of $C_8F_{17}$—$C_2H_4$—$SO_2$—NH—$CH_3$ having a melting point of 107°–109° C. were recovered.

The yield amounted to 86%.

EXAMPLE 11

32.3 g of $C_{10}F_{21}$—$C_2H_4$—$SO_2Cl$ was added to 100 cm³ of ethyl ether and to the constantly stirred mixture 7.5 l/h ammonia was added over a period of 2 hours. The temperature rose from 20° to 34° C. in 20 minutes and stabilized at this temperature for 20 minutes before gradually dropping to 23° C. Ethyl ether was removed by evaporation leaving a solid substance which was stirred with 300 cm³ of ethyl acetate. After filtration, a filtrate was recovered and concentrated to a volume of 60 cm³. Filtration yielded 26.8 g of solid matter which was recrystallized in 200 cm³ of a mixture of carbon tetrachloride (50% by volume) and ethyl acetate. In this manner 25.4 g of $C_{10}F_{21}$—$C_2H_4$—$SO_2$—$NH_2$ having a melting point of 173°–175° C. was recovered.

This sulfonamide was obtained with a yield of 81%.

EXAMPLE 12

18.7 g of $C_4F_9$—$(C_2H_4)_2$—$SO_2Cl$ was dissolved in 100 cm³ of ethyl ether and to the constantly stirred solution was added ammonia for 2 hours at a rate of 7.5 l/h. Immediately upon addition of the ammonia, a white, solid substance formed. The temperature rose from 20° to 84° C. in 30 minutes and stabilized at this temperature for 80 minutes before dropping gradually to 22° C. At this point 100 cm³ of ethyl ether was added and the resulting mixture was washed in water (four times with 25 cm³). The ethereal portion was then dried on anhydrous sodium sulfate and filtered whereupon the ethyl ether was evaporated. In this way, 17.1 g of solid matter was obtained which was recrystallized in 110 cm³ of carbon tetrachloride. 14.6 g of $C_4F_9$—$(C_2H_4)_2$—$SO_2$—$NH_2$ was isolated, having a melting point of 80°–82° C.

This sulfonamide was obtained with a yield of 82%.

EXAMPLE 13

114.8 g of $C_6F_{13}$—$(C_2H_4)_2SO_2Cl$ was dissolved in 500 cm³ of ethyl acetate and to the constantly stirred solution was added ammonia for 4 hours at a rate of 15 l/h. White solid matter formed immediately on introducing ammonia. The temperature rose from 20° to 35° C. in 30 minutes and stabilized at this temperature for 1½ hours before dropping gradually to 22° C. After the reaction the mixture was washed in water (4 times with 100 cm³) and dried on anhydous sodium sulfate, it was filtered and the solvent was evaporated. The solid matter recovered was recrystallized in 280 cm³ of a mixture of carbon tetrachloride (90% by volume) and ethyl acetate. In this manner, 97.3 g of $C_6F_{13}$—$(C_2H_4)_2$—$SO_2$—$NH_2$ was isolated.

A yield of 88% was obtained.

EXAMPLE 14

28.7 g of $C_8F_{17}$—$(C_2H_4)_2SO_2Cl$ was dissolved in 200 cm³ of ethyl acetate and to the constantly stirred solution ammonia was added for 2 hours at a rate of 7 l/h. The temperature rose from 20° to 34° C. in 15 minutes and was maintained at this value for 1.5 hours by cooling the reactor by means of a water bath. When the reaction was finished 100 cm³ of water was added to the reacting medium. This resulted in a phase separation, one phase being a liquid phase, the other a dense gelatinous phase.

The gelatinous phase was extracted 3 times with 100 cm³ portions of ethyl acetate and these extracts were collected with the liquid phase mentioned. The resulting solution was dried on anhydrous sodium sulfate and, after filtration, concentrated to 60 cm³. After filtration, 23.1 g of solid $C_8F_{17}$—$(C_2H_4)_2SO_2$—$NH_2$ having a melting point of 125°–127° C. was obtained.

This sulfonamide was isolated with a yield of 83%.

EXAMPLE 15

27.3 g of $C_8F_{17}$—$C_2H_4$—$SO_2Cl$ was dissolved in 200 cm³ of ethyl acetate and to the constantly stirred solution was added ammonia for 2 hours at a rate of 12 l/h. The reaction being exothermic, the temperature rose from 20° to 40° C. in 30 minutes and then dropped gradually. The reacting medium was then washed 4 times with 50 cm³ portions of water and the organic extracts dried on anhydrous sodium sulfate which was removed by filtration before evaporating the ethyl acetate in vacuum. In this way 25.5 g of solid matter was obtained which was recrystallized in 200 cm³ of a mixture of carbon tetrachloride (80% by volume) and ethyl acetate. 22.1 g of $C_8F_{17}$—$C_2H_4$—$SO_2$—$NH_2$ was isolated having a melting point of 143°–146° C.

The yield was 84%.

EXAMPLE 16

22.3 g of $C_6F_{13}$—$C_2H_4$—$SO_2Cl$ was dissolved in 100 cm³ of chloroform and to the constantly stirred solution was added ammonia for 2 hours at a rate of 12 l/h. The temperature rose from 22° to 41° C. in 30 minutes and then dropped gradually. 100 cm³ of ethyl acetate was then added to the reacting medium and the resulting mixture washed 4 times with 50 cm³ portions of water. The organic extracts were dried on anhydrous sodium sulfate which was later removed by filtration and the filtrate evaporated. In this manner 21.1 g of solid matter was recovered and recrystallized in 100 cm³ of a mixture of carbon tetrachloride (90% by volume) and ethyl acetate. 17.3 g of $C_6F_{13}$—$C_2H_4$—$SO_2$—$NH_2$ was isolated having a melting point of 92°–93° C.

This sulfonamide was obtained with a yield of 81%.

The preparation of polyfluorinated sulfonic chlorides based on oxidation of the chlorine from a polyfluorinated sulfocyanide $C_nF_{2n+1}$ (—$CH_2$—)$_b$ SCN was described in copending U.S. application Ser. No. 851,081 filed Aug. 18, 1969, assigned to the same assignee of this application. The oxidation of a polyfluorinated sulfocyanide having the formula

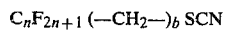

$C_nF_{2n+1}$ (—$CH_2$—)$_b$ SCN by chlorine or bromine is easily carried out when the sulfocyanide is dissolved in a suitable solvent as a reaction medium. It is preferred to use as a solvent a water-acetic acid mixture containing between 5 and 25% of the water by volume.

A reaction temperature between about 15° C. and 120° C., can generally be used, but it is preferred to use a reaction temperature between 15° C. and 75° C.

EXAMPLE I

Chlorine was bubbled to 20° for 3 h at the rate of 4 l/h through a mixture of $C_2F_5$—$C_2H_4$—SCN (20.5 g; 0.1 mole) glacial acetic acid (100 cm$^3$) and water (12 cm$^3$ at 20° C.) for 3 hours at the rate of 4 l/hour. After 1 hour and 45 minutes, the temperature rose to 61° C. in 15 minutes. It remained at this value for 15 minutes and then it gradually went down to the ambient temperature. The chlorine output was then stopped and the apparatus purged with a nitrogen flow for 30 minutes. A solid (4.1 g) was then filtered from the reaction mixture, the main constituent of which was ammonium chloride. The filtrate was distilled and 4 fractions and one residue were obtained as follows:

a—Fraction 54°–60°/100 mm, 58.1 g was composed of water and acetic acid b—Fraction 62°–5°/100 mm. Water (100 cm$^3$) was added to this fraction, and a dense phase was decanted (7.6 g) composed of water (2.4%), acetic acid (11.6%) and $C_2F_5$—$C_2H_4$—$SO_2Cl$ (85.8%; 29.6 mole)

c—Fraction 62°–92°/100 mm; 4.8 g was composed of $C_2F_5$—$C_2H_4$—Cl (1%), acetic acid (70%) and $C_2F_5$—$C_2H_4$—$SO_2Cl$ (29%; 12 mmole)

d—Fraction 92°–7°/100 mm; 6.5 g was composed of $C_2F_5$—$C_2H_4$—Cl (2.8%), $C_2F_5$—$C_2H_4$—$SO_2Cl$ (92.4%; 24.7 mmole), and three unidentified compounds (4.8%)

e—Solid residue, 3.2 g unidentified solid. $C_2F_5$—$C_2H_4$—$SO_2Cl$ was obtained with a conversion rate of 66.5%

EXAMPLE II

Chlorine at the rate of 4 l/hour was bubbled at 50° C. for 3 hours and 30 minutes through a mixture of $C_4F_9$—$C_2H_4$—SCN (30.5 g; 0.1 mole) glacial acetic acid (100 cm$^3$) and water (12 cm$^3$). After 30 minutes, the temperature rose to 75° C. and remained at this value for 30 minutes before gradually going down to the ambient temperature. After stopping the chlorine output, the apparatus was purged with a nitrogen flow for 30 minutes. A solid (3.9 g) was then filtered from the mixture, the main constituent of which was ammonium chloride. The filtrate was distilled; two fractions and one residue were obtained:

a—Fraction 50°–64°/100 mm, constituted of water and acetic acid b—Fraction 90°–95°/20 mm; 27.4 g composed of $C_4F_9$—$C_2H_4$—1 (3.4%), $C_4F_9$—$C_2H_4$—SCN (12.3%/10 mmole) and $C_4F_9$—C H—SO Cl 84.3%; 23.6 mmole)

c—Solid residue 4.6 g unidentified solid. $C_4F_9$—$C_2H_4$—$SO_2Cl$ was obtained with a conversion rate of 68% and a yield of 75.5%.

The preparation of polyfluorinated sulfocyanides is disclosed in U.S. patent application Ser. No. 795,063 filed Jan. 29, 1969, assigned to the same assignee of this application.

The perfluoroalkyl sulfocyanides of this invention are prepared by reacting at a temperature in the range between 0° and 250° C., and preferably between about 40° and 150° C., a perfluoroalkyl halide of the formula

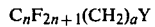

$C_nF_{2n+1}(CH_2)_aY$ wherein n is an integer from 1 to 20, a is an integer from 2 to 20, and Y is a chlorine, iodine or bromine atom, with a sulfocyanide of the formula M(SCN)$_b$ wherein M is hydrogen, the ammonium radical or a metal of the group IA, IB, IIA, IIB, or VIII of the periodic table, or aluminum or lead, and b is an integer equal to the valency of M.

Under certain conditions, it is advantageous to carry out the reaction under pressure. For instance, this will be the case when one or more physical properties of the solvent or of a reactant, such as its vapor pressure, renders this necessary or advisable. It is also preferred to operate in the presence of a solvent, but this is not obligatory. The solvent must be inert toward the reactants and should have a boiling point below approximately 250° C. Suitable solvents include:

I. A primary, secondary, or tertiary alcohol of 1 to 10 carbon atoms, such as ethanol, n-propanol, n-butanol, isopropanol, isobutanol, n-pentanol, isopentanol, n-hexanol, 2-heptanol and n-heptanol;

II. An aliphatic, cyclic, heterocyclic or aromatic ether, such as propyl and isopropyl ethers, dioxane, tetrahydrofuran, tetrahydropyrane, and anisole;

III. An aliphatic, cyclic or aromatic ketone, such as 2-butanone, 2-pentanone, 3-pentanone, cyclohexanone, and acetophenone;

IV. An aliphatic or aromatic ester such as propyl format methyl acetate, ethyl acetate, phenyl acetate, methyl benzoate, and ethyl benzoate;

V. A tertiary amine, such as trimethylamine, triethylamine, pyridine, 2-methylpyridine, and N-methylpiperidine;

VI. An aliphatic or aromatic nitrile, such for instance as acetonitrile, propionitrile, and benzonitrile;

VII. An aromatic hydrocarbon, such as benzene, a xylene, or toluene; and

VIII. A polar aprotic solvent, such for instance as dimethylformamide, dimethylsulfoxide, hexamethylphosphorotriamide, sulfolane, and nitrobenzene.

The following examples, which are not given by way of any limitation, illustrate the new compounds and their preparation pursuant to the invention of U.S. application Ser. No. 795,063. In all the examples, when a fraction contains several constituents, the mentioned percentages are molar percentages of the various compounds and the yields are calculated in relation to the starting fluorinated material.

EXAMPLE III

A mixture of 31 grams of KSCN and 80 cc of ethanol were heated to 78° C. under constant stirring. Then 74.8 grams of $C_4F_9$—$C_2H_4$—I were added within a period of 30 minutes, and when this addition had been achieved, the reaction mixture was kept at 78° C. for three hours. A solid comprising potassium iodide and unreacted potassium sulfocyanide was removed by filtration, and the filtrate was distilled to yield ethyl alcohol and two other fractions, to wit, 1. a fraction removed at 40° and /50 mm Hg. This fraction was washed with water, which yielded an organic phase (11.2 g) comprising $C_4F_9$—$C_2H_4I$ (88%), $C_4F_9$—$C_2H_4$—SCN (7.4%) and three impurities which could not be identified.

2. A fraction removed at 96° and 20 mm Hg, 45 g. This fraction comprised $C_4F_9$—$C_2H_4$—I (1%), $C_4F_9$—$C_2H_4$—SCN (97.8%) and three non-identified impurities (1.2%).

The conversion rate and the yield of $C_4F_9$—$C_2H_4$—SCN were about 73 and 85%, respectively.

EXAMPLE IV

There was heated to 78° C., with constant stirring, a mixture of KSCN (31 g) and 100 cc of ethanol. To this mixture was added 94.8 g of $C_6F_{13}$—$C_2H_4$—I over a period of 1½ hours, and when this addition had been made, the reaction medium was maintained at 78° C. for 4½ hours. Solid potassium iodide and unreacted potassium sulfocyanide were filtered off, and the filtrate was distilled to remove the ethyl alcohol and two fractions, to wit, 1. A fraction separated at 80° and 20 mm Hg, weighing 14 g. This fraction comprised $C_6F_{13}$—$C_2H_4$—I (78.4%), $C_6F_{13}$—$C_2H_4$—SCN (19.6%), and three non-identified impurities (2%).

2. A fraction separated between 121° and 122° C. at 20 mm Hg and weighing 53.5 g. This fraction contained 132 moles of $C_6F_{13}$—$C_2H_4$—SCN. The $C_6F_{13}$—$C_2H_4$—SCN is solid at room temperature and melts at approximately 35° C.

The conversion rate and the yield of $C_6F_{13}$—$C_2H_4$—SCN is 69 and 79%, respectively.

We claim:

1. A polyfluorinated sulfonamide compound having the structure

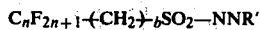

wherein
(a) $C_nF_{2n+1}$ corresponds to a straight or branched polyfluorinated carbon chain, n being a number of from 1 to 20;
(b) b is an integer of from 2 to 20;
(c) —NRR' is selected from the group (d) or (e) below:
(d) N is nitrogen; R is hydrogen or an alkyl radical of from 1 to 10 carbon atoms; and R' is hydrogen, an alkyl radical of from 1 to 10 carbon atoms, a cyclic alkyl radical of from 5 to 12 carbon atoms, or an aryl hydrocarbon radical of from 6 to 12 carbon atoms;
(e) —NRR' is a pyrrolidine radical having the structure

2. A polyfluorinated sulfonamide compound having the structure

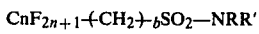

wherein
(a) $C_nF_{2n+1}$ corresponds to a straight or branched polyfluorinated carbon chain, n being a number of from 1 to 20;
(b) b is equal to 2 or 4;
(c) —NRR' is selected from the group (d) or (e) below:
(d) N is nitrogen; R is hydrogen or an alkyl radical of from 1 to 10 carbon atoms; and R' is hydrogen, an alkyl radical of from 1 to 10 carbon atoms, a cyclic alkyl radical of from 5 to 12 carbon atoms, or an aryl hydrocarbon radical of from 6 to 12 carbon atoms; or
(e) —NRR' is a pyrrolidine radical having the structure

* * * * *

UNITED STATES PATENT AND TRADEMARK OFFICE
CERTIFICATE OF CORRECTION

PATENT NO. : 4,296,034
DATED : October 20, 1981
INVENTOR(S) : Pierre Bouvet and Jean-Pierre Lalu It is certified that error appears in the above-identified patent and that said Letters Patent are hereby corrected as shown below:

Col. 2, line 25, change "7.1 l per hour" to

--7.5 l per hour--

Col. 5, line 34, change " to 84°C" to

--to 34°C--

Col. 5, line 34, change "for 80 minutes" to

--for 30 minutes--

Signed and Sealed this

Second Day of February 1982

[SEAL]

Attest:

GERALD J. MOSSINGHOFF

Attesting Officer

Commissioner of Patents and Trademarks